United States Patent [19]

Albisser

[11] Patent Number: 5,242,900
[45] Date of Patent: Sep. 7, 1993

[54] TREATMENT OF DIABETES USING PHOSPHORYLATED INSULIN

[76] Inventor: A. Michael Albisser, 52 Wendover Rd., Toronto, Ontario, Canada, M8X 2L3

[21] Appl. No.: 707,542

[22] Filed: May 30, 1991

[51] Int. Cl.⁵ ............... A61K 37/26; C07K 3/12; C07K 3/28
[52] U.S. Cl. ........................... 514/3; 530/303; 530/305
[58] Field of Search ............... 530/303, 305; 514/3

[56] References Cited

U.S. PATENT DOCUMENTS 3,869,437 3/1975 Lindsay et al. ............... 530/303
4,705,845 11/1987 Cerami et al. ............... 530/305

Primary Examiner—Michael G. Wityshyn
Assistant Examiner—Choon P. Koh
Attorney, Agent, or Firm—William H. Murray; Robert E. Rosenthal

[57] ABSTRACT

Phosphorylated insulins which can be prepared from chemically extracted pharmacological insulins by gentle treatment with phosphorus oxychloride, have been shown to have reduced bioactivity by mouse convulsion assay, but such phosphorylated insulins reduce hyperglycemia when administered to diabetic subjects without inducing hypoglycemia.

8 Claims, 5 Drawing Sheets

| | PORK | | HUMAN | | BEEF | | RAT 1 | | RAT 2 | | GUINEA PIG | | COYPU | |
|---|---|---|---|---|---|---|---|---|---|---|---|---|---|---|
| | A | B | A | B | A | B | A | B | A | B | A | B | A | B |
| 1 | GLY | PHE | GLY | PHE | GLY | PHE | GLY | PHE | GLY | PHE | GLY | PHE | GLY | TYR |
| 2 | ILE | VAL | ILE | VAL | ILE | VAL | ILE | VAL | ILE | VAL | ILE | VAL | ILE | VAL |
| 3 | VAL | ASN | VAL | ASN | VAL | ASN | VAL | LYS | VAL | LYS | VAL | SER | VAL | SER |
| 4 | GLU | GLN | GLU | GLN | GLU | GLN | ASP | GLN | GLU | GLN | ASP | ARG | ASP | GLN |
| 5 | GLN | HIS | GLN | HIS | GLN | HIS | GLN | HIS | GLN | HIS | GLN | HIS | GLN | ARG |
| 6 | CYS | LEU | CYS | LEU | CYS | LEU | CYS | LEU | CYS | LEU | CYS | LEU | CYS | LEU |
| 7 | CYS | CYS | CYS | CYS | CYS | CYS | CYS | CYS | CYS | CYS | CYS | CYS | CYS | CYS |
| 8 | THR | GLY | THR | GLY | THR | GLY | ALA | GLY | ALA | GLY | THR | GLY | THR | GLY |
| 9 | SER | SER | SER | SER | SER | SER | SER | PRO | SER | SER | GLY | SER | ASN | SER |
| 10 | ILE | HIS | ILE | HIS | VAL | HIS | ILE | HIS | ILE | HIS | THR | ASN | ILE | GLN |
| 11 | CYS | LEU | CYS | LEU | CYS | LEU | CYS | LEU | CYS | LEU | CYS | LEU | CYS | LEU |
| 12 | SER | VAL | SER | VAL | SER | VAL | SER | VAL | SER | VAL | THR | VAL | SER | VAL |
| 13 | LEU | GLU | LEU | GLU | LEU | GLU | LEU | GLU | LEU | GLU | ARG | GLU | ARG | ASP |
| 14 | TYR | ALA | TYR | ALA | TYR | ALA | TYR | ALA | TYR | ALA | HIS | THR | ASN | THR |
| 15 | GLN | LEU | GLN | LEU | GLN | LEU | GLN | LEU | GLN | LEU | GLN | LEU | GLN | LEU |
| 16 | LEU | TYR | LEU | TYR | LEU | TYR | LEU | TYR | LEU | TYR | LEU | TYR | LEU | TYR |
| 17 | GLU | LEU | GLU | LEU | GLU | LEU | GLU | LEU | GLU | LEU | GLN | SER | MET | SER |

CONTINUED FROM FIG. 1A

|    |     |     |     |     |     |
|----|-----|-----|-----|-----|-----|
| 18 | ASN VAL | ASN VAL | ASN VAL | SER VAL | SER VAL |
| 19 | TYR CYS | TYR CYS | TYR CYS | TYR CYS | TYR CYS |
| 20 | CYS GLY | CYS GLY | CYS GLY | CYS GLN | CYS ARG |
| 21 | ASN GLU | ASN GLU | ASN GLU | ASN ASP | ASN HIS |
| 22 | ARG | ARG | ARG | ASP | ASP |
| 23 | GLY | GLY | GLY | GLY | ARG GLY |
| 24 | PHE | PHE | PHE | PHE | PHE |
| 25 | PHE | PHE | PHE | PHE | TYR |
| 26 | TYR | TYR | TYR | TYR | ARG |
| 27 | THR | THR | THR | ILE | PRO |
| 28 | PRO | PRO | PRO | PRO | ASN |
| 29 | LYS | LYS | LYS | LYS | ASP |
| 30 | ALA | ALA | SER | ASP | *** |

TREATMENT OF DIABETES USING PHOSPHORYLATED INSULIN

FIELD OF INVENTION

This invention relates to the treatment of diabetes and novel forms of insulin therefor.

BACKGROUND OF INVENTION AND PRIOR ART

Since its first extraction by Banting and Best in 1921, insulin has been administered to countless thousands of diabetic patients with dramatic and life-saving effects. Not surprisingly, insulin has been intensively studied over the succeeding seventy years as a model peptide and elucidation of its crystallographic structure, peptide sequence, radio ligand assay and chemical synthesis represent major achievements in the history of molecular biology. Despite all of the work which has been done, the original method for self administration of insulin, namely subcutaneous injection, persists to this day and it is widely assumed it is this non-physiological route that results in the well known very poor control of blood glucose. It is also well known that when extracted insulins are injected hypoglycemia is readily produced by a small overdose, whereas when natural insulin delivery is restored to a diabetic patient, such as by pancreatic or Islet of Langerhans cell transplantation, hypoglycemia is not a problem. It appears, therefore, that while extracted insulins are very similar to natural insulins, they are not, in fact, the same. Indeed, over the years, the standard assay (mouse convulsion assay) to determine the potency of an extracted (pharmacological) insulin measures the amount of insulin necessary to induce rapid hypoglycemia in a typical normal animal whereas hypoglycemia is not produced at all with native (indogenous) insulin. By this assay, therefore, endogenous insulin could be said to be nonpotent.

The present inventor hypothesizes that the chemical extraction process commonly employed to obtain insulin from recombinant sources or from bovine or porcine pancreas denatures or degrades the native (indogenous) insulin or that the handling of the pharmacological insulin in some measure degrades the material. It is interesting to note that Banting and Best, in 1921, reported one water solubilized extract which normalized blood sugar in a diabetic dog but did not produce hypoglycemia and which was subsequently abandoned as unproductive, in favour of more vigorous chemical extractions with a more potent hypoglycemic action. Apparently Banting and Best did not appreciate the significance of their results which indicate to the present inventor that some subtle degradation of indogenous insulin occurs during chemical extraction in normal animals.

Following major studies into the human biochemical fuel cycle and many of the constituent substrate-hormonal interdependencies using a comprehensive metabolic simulator which included details of the energy cycles of carbohydrate-, protein-, and fat- derived fuel substrates, the inventor herein postulates that the chemical production of pharmacological insulin strips phosphate groups from the outer surfaces of the insulin molecule from residues widely known to be phosphorylatable and that phosphorylation of chemically extracted insulin is capable of producing an insulin which (a) will not invoke hypoglycemia in normal subjects (b) will reduce hyperglycemia in diabetic subjects but only to normal levels and (c) is not dose-response dependent.

Phosphorylation of amino acids, proteins and peptides including insulin is not novel. Attention is directed to U.S. Pat. No. 4,705,845 issued 10 November 1987, but such modified insulins retain about 85% of the bioactivity of the unphosphorylated starting material and hence induce hypoglycemia in diabetic and non-diabetic subjects. Clearly such phosphorylated materials contain a considerable amount of unreacted or degraded material.

OBJECT OF THE INVENTION

Thus, it is an object of the present invention to provide a novel, substantially pure phosphorylated product which will not invoke hypoglycemia in normal subjects and will reduce hyperglycemia in diabetic subjects to normal levels. Another object of the present invention is to provide a process for making novel insulins.

BRIEF STATEMENT OF INVENTION

By one aspect of the present invention there is provided a substantially pure phosphorylated insulin, for use in the treatment of diabetes, which reduces hyperglycemia without inducing hypoglycemia when administered to a diabetic subject.

By another aspect of this invention there is provided a method for producing a phosphorylated insulin which reduces hyperglycemia without inducing hypoglycemia when administered to a diabetic subject, said method comprising:

(a) dissolving a selected extracted insulin in a mixture of dry dimethyl formamide and concentrated phosphoric acid;

(b) adding phosphorus trichloride oxide and agitating said mixture at a temperature below about 10° C.;

(c) adjusting pH to about 7.4;

(d) centrifuging said solution and recovering a supernate;

(e) dialyzing said supernate against ammonium chloride so as to remove salt;

(f) separating by iso-electric focussing;

(g) purifying by ion exchange chromatography;

(h) isolating a phosphorylated insulin product by lyophilization.

By yet another aspect of this invention there is provided a method of treating diabetes mellitus without inducing hypoglycemia comprising administering to a diabetic subject an effective amount of a substantially pure phosphorylated insulin so as to reduce hyperglycemia and maintain normoglycemia.

DETAILED DESCRIPTION OF PREFERRED EMBODIMENTS

Figure 1B:
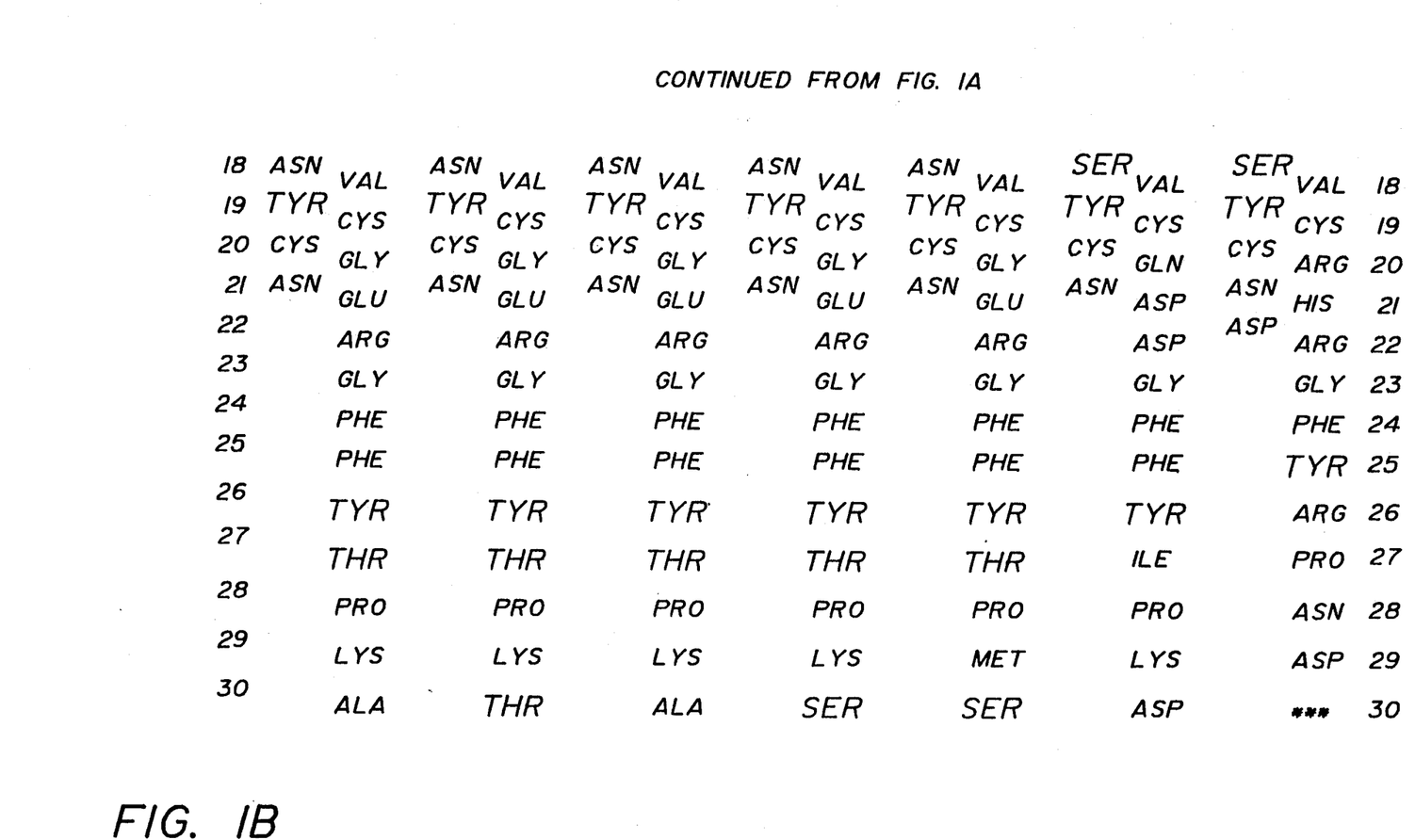
FIG. 1 is a chart showing the amino acid sequences of various mammalian insulins.
Figure 2:
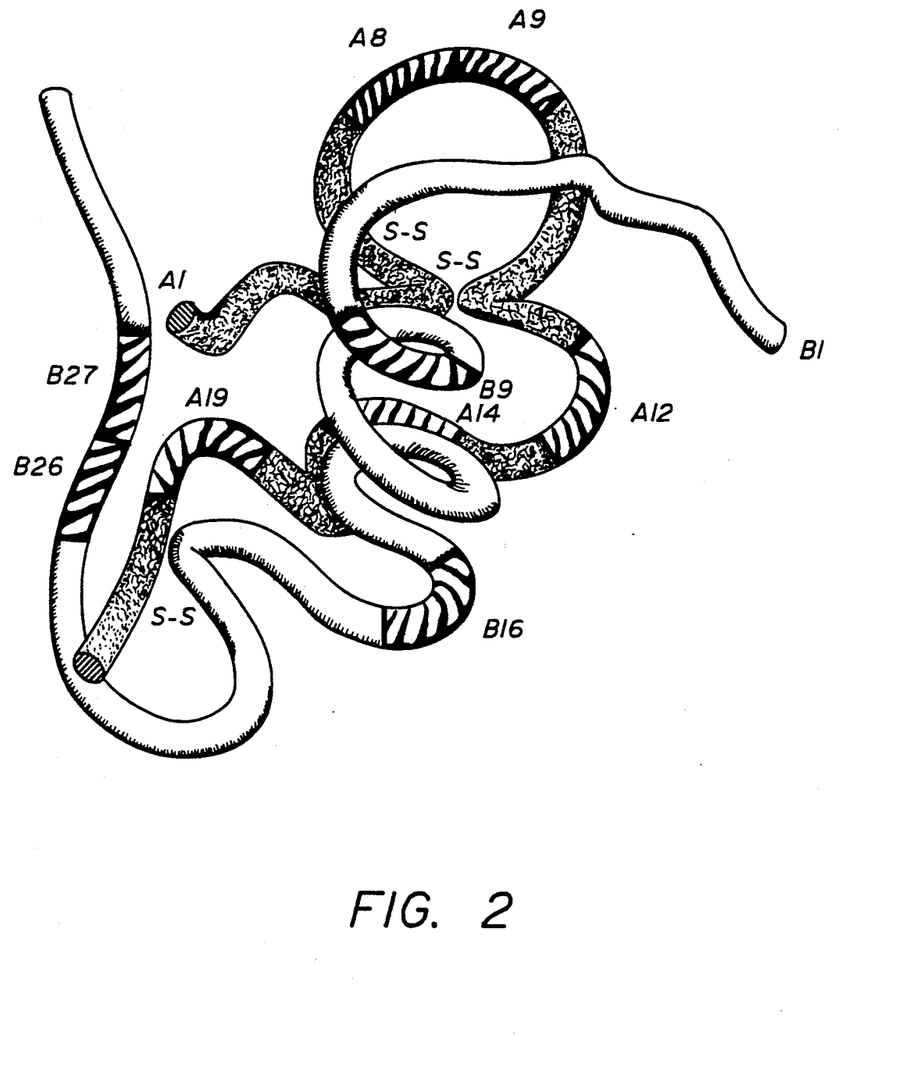
FIG. 2 is a schematic sketch of the amino acid structure of porcine insulin.

The amino acid sequences for the A and B chains of a number of mammalian insulins are shown in FIG. 1. Given that phosphate groups may only be substituted on Ser, Thr and Tyr residues, it can be seen that mammalian insulins have between 8 and 11 residues where phosphate groups may be substituted. Serine residues at B9 and A12 are conserved, except that substitution of the threonine at A12 in Guinea Pig is equivalent to a serine residue at that position insofar as phosphorylation is concerned. For porcine insulin, all the possible binding sites are illustrated in FIG. 2. Structurally, those at A8, A9, A12 and B9 are spatially most geometrically defined because of their proximity to the inter- and intra-molecular disulphide bridges as shown.

Energy minimization calculations indicate no major changes from the starting configuration of porcine insulin when substituted at all three serine residues. Root mean square displacements from the initial conformation are detailed in Table 1.

TABLE 1

Phosphorylation of Insulin: Root Mean Square Displacements from Initial Conformation

|  | Angstrom Units |
|---|---|
| All atoms | 1.421 |
| Backbone | 1.019 |
| Residue B9 | 0.713 |
| Residue A9 | 0.294 |
| Residue A12 | 0.340 |

The specific locations of the three serine residues (A9, A12, B9) in the A and B chains clearly place the added phosphate groups at the exposed surfaces of the prominent loops formed by the two overlapping (inter- and intra-chain) disulphide bridges (FIG. 2). This raises the likelihood that other structures, which may be similar to mammalian insulins but which may have other biocompatible polymer or amino acid backbones and which may or may not be peptides, may be synthesized according to coordinates derived from energy minimization principles, such that one or more phosphate groups are precisely located on the surface of the molecule and which would have similar bioactivity. Such compounds could be made orally acceptable using known techniques.

It is known that polar amino acid residues with aliphatic or aromatic hydroxyl groups can be phosphorylated both enzymatically and chemically. Using the chemical route it is somewhat easier to separate and purify the resulting crude material, and consequently this is the preferred route. Early workers attempting to phosphorylate insulin reported a product with 38% of the biological activity of the original, using the mouse convulsion assay, but apparently did not test it in diabetic animals. The investigators attributed the reduced bioactivity to damage to the peptide chain. In U.S. Pat. No. 4,705,845 a phosphorylation process is described in which insulin was dissolved in an organic solvent and reacted at reduced temperature with concentrated phosphoric acid to yield a product having 85% of the bioactivity of the unmodified insulin. This minimized supposed damage to the peptide chain and reduced the dephosphorylation which occurs at low pH.

EXAMPLE 1

Method for making phosphorylated insulin 20 mg of porcine insulin (Connaught-Novo, Toronto) was dissolved in a 4° C. mixture of 950 µl dry dimethylformamide (DMF) and 50 µl of concentrated phosphoric acid which was prepared by heating 85% aqueous phosphoric acid at 160° C. for 5 hours. 5 µl of $POCl_3$ (phosphorous trichloride oxide) dissolved in 15 µl DMF was added and the mixture was shaken at 4° C. overnight. Approximately 1 ml cracked ice was added and the pH adjusted to 7.4 with 10N NaOH. The solution was brought to 5 ml and centrifuged. The supernate was extensively dialyzed against 50 mM ammonium bicarbonate pH 7.5 to remove salt and then separated by iso-electric focusing. Samples were purified by ion-exchange chromatography and isolated after gel filtration by lyophilization from the ammonium bicarbonate solution. Insulin concentration was determined by immunoassay. Only separated samples with multiple (3 or 5) negatively charged adducts were used. Characteristically the modified product was intact, monomeric insulin with about 5-10% being unmodified, according to the chromatographs. The crude products were readily soluble in water at neutral pH. In order to prolong its biological action times, protamine was added to complex with the phosphorylated insulin and thereby to reduce its rate of vascular entry because of aggregate size.

The phosphorylated insulin produced in Example 1 was extensively tested in laboratory dogs. The dog is an excellent model for human metabolism. Pancreatectomy makes it metabolically unstable, with difficult to regulate glycemia while critically dependent on daily exogenous insulin replacement. Glycemia is very difficult to stabilize when conventional methods are used and even when extracted insulin is pumped intravenously and continuously all according to open-loop control methods. Small changes of a few percent in the delivery rates of extracted insulin have major effects on fasting glycemia. Although normal blood glucose levels can be achieved in this model using a closed-loop artificial endocrine pancreas instrument, the decline of blood glucose into hypoglycemia almost always has to be averted by co-infusions of dextrose or glucagon, even if pancreatic or extra-pancreatic glucagon is present. With careful selection of the parameters in the specific algorithms, normoglycemia can be achieved and maintained, but this is not robust. Any over-insulinizing of the subject immediately provokes the need for such counter-regulatory co-infusions.

EXAMPLE 2

Animal Studies

Nine dogs of initially normal body weight were studied in accordance with Institutional Guidelines for animal experiments. Exteriorized, indwelling catheters were placed for intra-portal insulin administration and peripheral venous blood sampling. All were studied initially as normals. Subsequently all were pancreatectomized; five were autografted and the remaining four were treated pharmacologically both with the modified insulins described above in Example 1 and the corresponding unmodified conventional extracted insulins. Small venous blood samples were drawn via the indwelling blood sampling catheter at 30-60 minute intervals for plasma glucose determination in the subcutaneous experiments and at $-10,0,3,6,10,20,30,60$ minutes in the intravenous experiments. Intraportal dosages of regular porcine insulin unless otherwise specified were standardized at 210 pMol/kg (0.03U/kg) body weight and $200\pm40$ pMol/kg of phosphorylated insulin. All animals were conscious and ambulatory during the studies.

At the conclusion of experimental protocols, it was verified that all nine of the animals were diabetic by extirpating the grafts (from the transplant recipients) or withdrawing insulin therapy (from the pancreatectomized animals). In all cases, rapidly evolving hyperglycemia became life-threatening. For survival, insulin treatment had to be re-initiated.

Plasma glucose was determined using a glucose analyzer (Beckman Instruments, Fullerton, CA). IRI was assayed using porcine insulin standard and $^{125}$I porcine insulin tracer (Novo Research Institute, Gentofte, Denmark), antiserum and a dextran-coated charcoal separation technique (Albisser et al, Diabetes 35:97-100, 1986). In the studies using porcine phosphorylated insulin, the above assay was performed as for porcine insulin, but using equimolar standards of phosphorylated insulin. Parallel standard curves were obtained. Plasma samples when diluted gave values that fell along the phosphorylated insulin standard curve. All values were expressed as mean $\pm$SEM unless otherwise indicated.

INTRAVENOUS STUDIES

Figure 3:
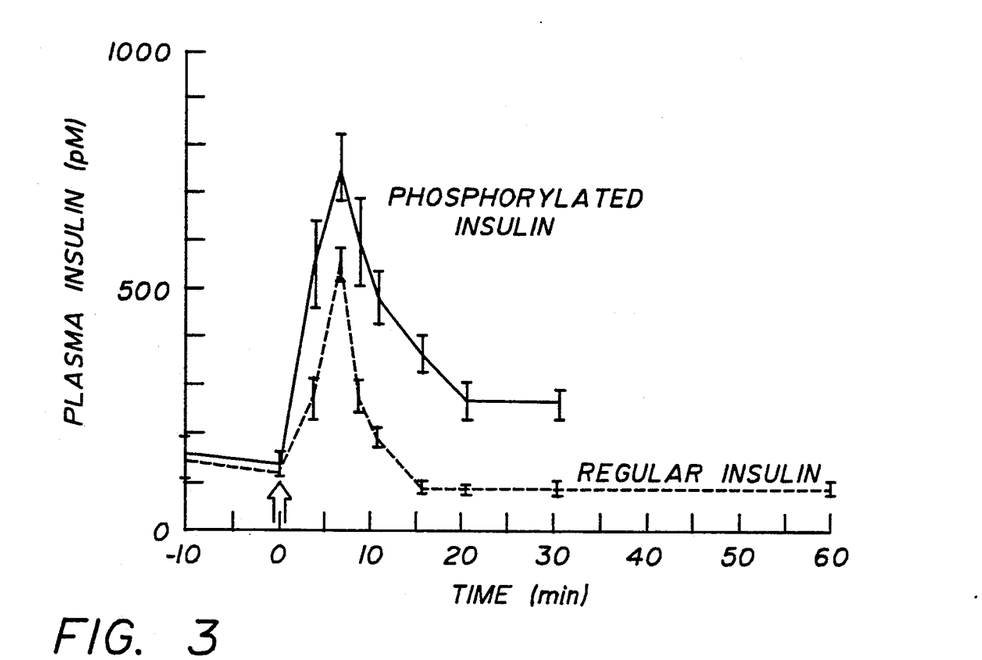
FIG. 3 is a graph showing plasma insulin after injection of regular and phosphorylated insulin, against time.
Figure 4:
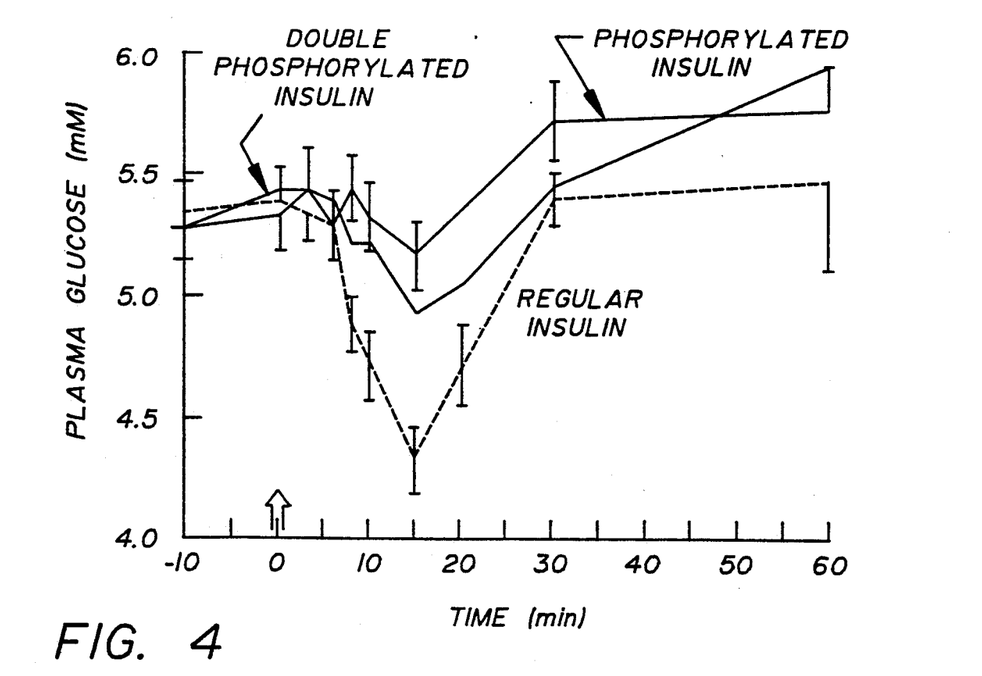
FIG. 4 is a graph showing plasma glucose after injection of regular and phosphorylated insulin against time.

FIGS. 3 and 4 demonstrate that in the normal dog, intra-portal administration of phosphorylated insulin has a minor effect on blood glucose (FIG. 4), despite the expected increases in measured plasma insulin concentration (FIG. 3). At 15 minutes this minor drop of 0.2 mM reflects the presence of the small proportion (5-10%) of unphosphorylated insulin in the crude preparations used in these studies. Control studies with similar amounts of purified porcine regular insulin showed the expected insulinemia and hypoglycemia characteristic of this extract and route of administration. Yet, even a 2-fold larger dose of phosphorylated insulin is without major hypoglycemic effect.

SUBCUTANEOUS STUDIES

Figure 5:
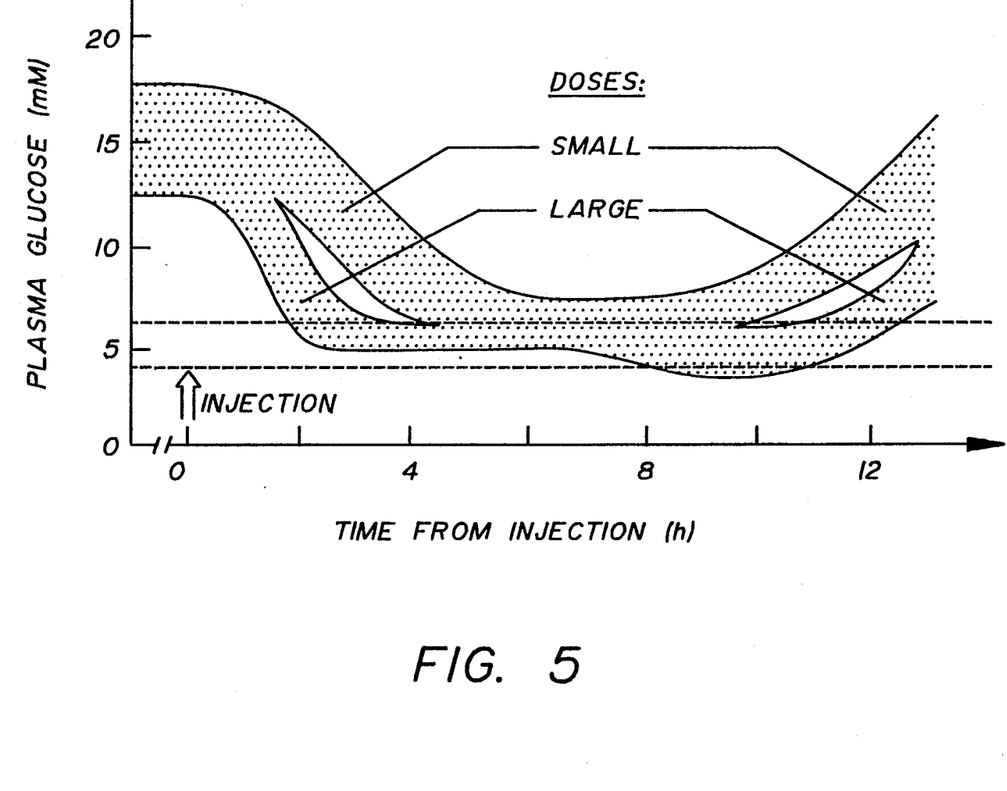
FIG. 5 is a graph illustrating plasma glucose levels with time after injection of different doses of phosphorylated insulin.

Subsequent to pancreatectomy the animals were studied repeatedly, now in the post-absorptive, hyperglycemic state of 14-20 mM, because the conventional insulin depot administered the previous day had become depleted. These experiments indicated that over an approximately 5-fold range of 30-150 nMol, phosphorylated insulin was adequate to lower blood glucose concentrations and to maintain euglycemia for 2-6 hours in the fasted animal. As shown in FIG. 5, when crudely phosphorylated insulin was injected subcutaneously at time zero (about 0900h), small specific doses of approximately 4 nMol/kg lowered plasma glucose to the normal range of 4.5-6.0 mM. When 4-fold larger doses were given, the effect occurred more rapidly and lasted longer. Early hypoglycemia never occurred, but there was a delayed tendency to levels beneath the normal range with greater than 4-fold larger doses. Similar relative effects occurred consistently regardless of the starting plasma glucose concentration. It is important to recognize that a 4-fold larger dose of regular (unphosphorylated) insulin could be fatal to the dog.

Repeating the smaller dosage injections of phosphorylated insulin at 6-8h intervals (not shown) served to maintain plasma glucose in the range normal for postabsorptive dogs (shown here as the stippled area). Animals treated with twice daily injections using split dosages of regular phosphorylated insulin and protamine complexed phosphorylated insulin were easily maintained before and after meals within the normal range of glycemia (4.5-6.0mM) for extended periods, up to 30 days. With continued treatment, all animals developed palpable fat-like deposits in the areas of repeated subcutaneous injections with phosphorylated insulins. Such lipo-genesis was not observed in animals similarly injected for periods of 1-3 years but with purified porcine conventional insulins.

In contrast to the marginal stability achievable with the injection or infusion of extracted insulins, auto-transplantation of the canine pancreas immediately reversed the diabetes. In the experiments herein it robustly normalized the blood glucose concentrations and ameliorated the metabolic states of the five recipients even though the route of administration was peripheral rather than portal and the amount of pancreas grafted was variable. Hypoglycemia never occurred. The results were similar to those obtained with phosphorylated insulin simply injected subcutaneously.

The liver is known to extract about half of the insulin presented to it on the first pass. Apparently phosphorylated insulin is not extracted to the same extent. This results in the higher peripheral concentrations at the peak and the slower decline to fasting levels observed with phosphorylated insulin (FIG. 4). Despite the almost two-fold higher phosphorylated insulin concentrations in the periphery, plasma glucose levels are essentially unaffected. The prompt and powerful plasma glucose lowering effect of regular, unphosphorylated insulin is clearly demonstrated. In choosing the amount of regular insulin to be used, attempts are made to keep the nadir in glucose levels precisely within the physiological range. However as phosphorylated insulin does not provoke the same drop in plasma glucose levels, on one occasion a double dosage was administered (solid line FIG. 4). This provokes a small decrease in plasma glucose (about 0.5mM) that is consistent with the effects of a small fraction of unphosphorylated insulin in the phosphorylated material.

Extracted insulins do not robustly stabilize diabetes, when delivered by intensive conventional methods (including multiple daily subcutaneous injections or continuous intravenous infusions), but only when delivered intravenously by a closed-loop feedback system responding to minute-by-minute blood glucose measurements. However phosphorylated insulins do robustly stabilize diabetes, even when widely different amounts are administered subcutaneously and independently of any closed-loop blood glucose control system. In the animal experiments reported herein, phosphorylated insulin exhibits effects entirely consistent with all of the predictions made for it. Experimentally, even crude chemical phosphorylation of extracted insulin restored to it many if not all of the hypothetically ideal biological characteristics of natural insulin: (i) it had no immediate hypoglycemic effect when blood glucose levels were in the normal range, only when glucose levels were well above normal; (ii) it enabled the metabolic regulatory mechanism to proceed and stable normal glycemia resulted almost independently of dosing, even when administered subcutaneously; (iii) it certainly had (macroscopic) anti-lipolytic effects, as evidenced by the lipogenesis in the injection areas. Parenthetically, these animals also showed a tendency to regain body weight (1-3kg) lost following pancreatectomy—a process unachievable with on-going management using extracted insulins.

---

I claim:

1. A substantially pure phosphorylated insulin, for use in the treatment of diabetes, which reduces hyperglycemia without inducing hypoglycemia when administered to a diabetic subject.

2. A substantially pure phosphorylated insulin as claimed in claim 1 containing at least three phosphate groups.

3. A substantially pure phosphorylated insulin as claimed in claim 2 wherein three of said phosphate groups are substituted at serine residues in said insulin.

4. A substantially pure phosphorylated insulin as claimed in claim 3 additionally phosphorylated at threonine residues in said insulin.

5. A substantially pure phosphorylated insulin as claimed in claim 4 additionally phosphorylated at tyrosine residues in said insulin.

6. A method for producing a phosphorylated insulin which reduces hyperglycemia without inducing hypoglycemia when administered to a diabetic subject, said method comprising:

(a) dissolving a selected extracted insulin in a mixture of dry dimethyl formamide and concentrated phosphoric acid;
(b) adding phosphorus trichloride oxide and agitating said mixture at a temperature below about 10° C.;
(c) adjusting pH to about 7.4;
(d) centrifuging said solution and recovering a supernate;
(e) dialyzing said supernate against ammonium chloride so as to remove salt;
(f) separating by iso-electric focussing;
(g) purifying by ion exchange chromatography;
(h) isolating a phosphorylated insulin product by lyophilization.

7. A method of treating diabetes mellitus without inducing hypoglycemia comprising administering to a diabetic subject an effective amount of a substantially pure phosphorylated insulin so as to reduce hyperglycemia and to maintain normoglycemia.

8. A method as claimed in claim 7 wherein said phosphorylated insulin is administered by subcutaneous injection.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
    ( A ) LENGTH: 51 residues
    ( B ) TYPE: amino acids
    ( C ) STRANDEDNESS: double
    ( D ) TOPOLOGY: linear ( i i ) MOLECULE TYPE: peptide ( i i i ) HYPOTHETICAL: no ( i v ) ORIGINAL SOURCE:
    ( A ) ORGANISM: Pig pancreas ( i x ) FEATURE:
    ( D ) OTHER INFORMATION: Peptide has two subunits. Second
       subunit starts at position 22. Cys-Cys cross links
       between positions 6 and 11, 7 and 28, and 20 and 40.
       One or more of the Serine and/or Threonine residues
       are phosphorylated as O-phosphates.

( x i ) SEQUENCE DESCRIPTION: SEQ ID NO:1:

Gly Ile Val Glu Gln Cys Cys Thr Ser Ile Cys Ser Leu Tyr Gln
1               5                   10                  15

Leu Glu Asn Tyr Cys Asn Phe Val Asn Gln His Leu Cys Gly Ser
16              20                  25                  30

His Leu Val Glu Ala Leu Tyr Leu Val Cys Gly Glu Arg Gly Phe
31              35                  40                  45

Phe Tyr Thr Pro Lys Ala
46              50

( 2 ) INFORMATION FOR SEQ ID NO:2:

( i ) SEQUENCE CHARACTERISTICS:
    ( A ) LENGTH: 51 residues
    ( B ) TYPE: amino acids
    ( C ) STRANDEDNESS: double
    ( D ) TOPOLOGY: linear ( i i ) MOLECULE TYPE: peptide ( i i i ) HYPOTHETICAL: no ( i v ) ORIGINAL SOURCE:
    ( A ) ORGANISM: Human pancreas ( i x ) FEATURE:
    ( D ) OTHER INFORMATION: Peptide has two subunits. Second
       subunit starts at position 22. Cys-Cys cross links
       between positions 6 and 11, 7 and 28, and 20 and 40.
       One or more of the Serine and/or Threonine residues
       are phosphorylated as O-phosphates.

( x i ) SEQUENCE DESCRIPTION: SEQ ID NO:2:

Gly Ile Val Glu Gln Cys Cys Thr Ser Ile Cys Ser Leu Tyr Gln
1               5                   10                  15

Leu Glu Asn Tyr Cys Asn Phe Val Asn Gln His Leu Cys Gly Ser
16              20                  25                  30

His Leu Val Glu Ala Leu Tyr Leu Val Cys Gly Glu Arg Gly Phe
31              35                  40                  45

Phe Tyr Thr Pro Lys Thr 46      50

(2) INFORMATION FOR SEQ ID NO:3:

(i) SEQUENCE CHARACTERISTICS:
        (A) LENGTH: 51 residues
        (B) TYPE: amino acids
        (C) STRANDEDNESS: double
        (D) TOPOLOGY: linear     (ii) MOLECULE TYPE: peptide     (iii) HYPOTHETICAL: no     (iv) ORIGINAL SOURCE:
        (A) ORGANISM: Cattle pancreas     (ix) FEATURE:
        (D) OTHER INFORMATION: Peptide has two subunits. Second subunit starts at position 22. Cys-Cys cross links between positions 6 and 11, 7 and 28, and 20 and 40. One or more of the Serine and/or Threonine residues are phosphorylated as O-phosphates.

(xi) SEQUENCE DESCRIPTION: SEQ ID NO:3:

Gly Ile Val Glu Gln Cys Cys Ala Ser Val Cys Ser Leu Tyr Gln
1               5                   10                  15

Leu Glu Asn Tyr Cys Asn Phe Val Asn Gln His Leu Cys Gly Ser
16              20                  25                  30

His Leu Val Glu Ala Leu Tyr Leu Val Cys Gly Glu Arg Gly Phe
31              35                  40                  45

Phe Tyr Thr Pro Lys Ala
46              50

(2) INFORMATION FOR SEQ ID NO:4:

(i) SEQUENCE CHARACTERISTICS:
        (A) LENGTH: 51 residues
        (B) TYPE: amino acids
        (C) STRANDEDNESS: double
        (D) TOPOLOGY: linear     (ii) MOLECULE TYPE: peptide     (iii) HYPOTHETICAL: no     (iv) ORIGINAL SOURCE:
        (A) ORGANISM: rat 1 pancreas     (ix) FEATURE:
        (D) OTHER INFORMATION: Peptide has two subunits. Second subunit starts at position 22. Cys-Cys cross links between positions 6 and 11, 7 and 28, and 20 and 40. One or more of the Serine and/or Threonine residues are phosphorylated as O-phosphates.

(xi) SEQUENCE DESCRIPTION: SEQ ID NO:4:

Gly Ile Val Asp Gln Cys Cys Ala Ser Ile Cys Ser Leu Tyr Gln
1               5                   10                  15

Leu Glu Asn Tyr Cys Asn Phe Val Lys Gln His Leu Cys Gly Pro
16              20                  25                  30

His Leu Val Glu Ala Leu Tyr Leu Val Cys Gly Glu Arg Gly Phe
31              35                  40                  45

Phe Tyr Thr Pro Lys Ser
46              50

(2) INFORMATION FOR SEQ ID NO:5:

(i) SEQUENCE CHARACTERISTICS:
        (A) LENGTH: 51 residues
        (B) TYPE: amino acids
        (C) STRANDEDNESS: double (D) TOPOLOGY: linear (ii) MOLECULE TYPE: peptide (iii) HYPOTHETICAL: no (iv) ORIGINAL SOURCE:
    (A) ORGANISM: rat 2 pancreas (ix) FEATURE:
    (D) OTHER INFORMATION: Peptide has two subunits. Second subunit starts at position 22. Cys-Cys cross links between positions 6 and 11, 7 and 28, and 20 and 40. One or more of the Serine and/or Threonine residues are phosphorylated as O-phosphates.

(xi) SEQUENCE DESCRIPTION: SEQ ID NO:5:

```
Gly Ile Val Glu Gln Cys Cys Ala Ser Ile Cys Ser Leu Tyr Gln
 1               5                  10                  15

Leu Glu Asn Tyr Cys Asn Phe Val Lys Gln His Leu Cys Gly Ser
16              20                  25                  30

His Leu Val Glu Ala Leu Tyr Leu Val Cys Gly Glu Arg Gly Phe
31              35                  40                  45

Phe Tyr Thr Pro Met Ser
46              50
```

(2) INFORMATION FOR SEQ ID NO:6:

(i) SEQUENCE CHARACTERISTICS:
        (A) LENGTH: 51 residues
        (B) TYPE: amino acids
        (C) STRANDEDNESS: double
        (D) TOPOLOGY: linear     (ii) MOLECULE TYPE: peptide     (iii) HYPOTHETICAL: no     (iv) ORIGINAL SOURCE:
        (A) ORGANISM: Guinea pig pancreas     (ix) FEATURE:
        (D) OTHER INFORMATION: Peptide has two subunits. Second subunit starts at position 22. Cys-Cys cross links between positions 6 and 11, 7 and 28, and 20 and 40. One or more of the Serine and/or Threonine residues are phosphorylated as O-phosphates.

(xi) SEQUENCE DESCRIPTION: SEQ ID NO:6:

```
Gly Ile Val Asp Gln Cys Cys Thr Gly Thr Cys Thr Arg His Gln
 1               5                  10                  15

Leu Gln Ser Tyr Cys Asn Phe Val Ser Arg His Leu Cys Gly Ser
16              20                  25                  30

Asn Leu Val Glu Thr Leu Tyr Ser Val Cys Gln Asp Asp Gly Phe
31              35                  40                  45

Phe Tyr Ile Pro Lys Asp
46              50
```

(2) INFORMATION FOR SEQ ID NO:7:

(i) SEQUENCE CHARACTERISTICS:
        (A) LENGTH: 51 residues
        (B) TYPE: amino acids
        (C) STRANDEDNESS: double
        (D) TOPOLOGY: linear     (ii) MOLECULE TYPE: peptide     (iii) HYPOTHETICAL: no     (iv) ORIGINAL SOURCE:
        (A) ORGANISM: Coypu pancreas -continued (ix) FEATURE:
 (D) OTHER INFORMATION: Peptide has two subunits. Second
 subunit starts at position 23. Cys-Cys cross links
 between positions 6 and 11, 7 and 29, and 20 and 41.
 One or more of the Serine and/or Threonine residues
 are phosphorylated as O-phosphates.

(xi) SEQUENCE DESCRIPTION: SEQ ID NO:7:

```
Gly  Ile  Val  Asp  Gln  Cys  Cys  Thr  Asn  Ile  Cys  Ser  Arg  Asn  Gln
 1                   5                        10                       15

Leu  Met  Ser  Tyr  Cys  Asn  Asp  Tyr  Val  Ser  Gln  Arg  Leu  Cys  Gly
16                  20                        25                       30

Ser  Gln  Leu  Val  Asp  Thr  Leu  Tyr  Ser  Val  Cys  Arg  His  Arg  Gly
31                  35                        40                       45

Phe  Tyr  Arg  Pro  Asn  Asp
46                  50
```